United States Patent [19]

Nicolaou et al.

[11] Patent Number: 5,183,942

[45] Date of Patent: Feb. 2, 1993

[54] TEN-MEMBERED RING ENEDIYNEDIOLS AND ENEDIYNEDIONES HAVING DNA CLEAVING PROPERTIES

[75] Inventors: Kyriacos C. Nicolaou; Erik Sorensen, both of La Jolla; Chan-Kou Hwang, San Diego, all of Calif.; Robert Discordia, Liverpool, N.Y.; Robert G. Bergman, Kensington; Robert E. Minto, Albany, both of Calif.

[73] Assignee: The Scripps Research Institute, La Jolla, Calif.

[21] Appl. No.: 788,161

[22] Filed: Nov. 5, 1991

[51] Int. Cl.$^5$ .................. C07C 49/105; C07C 35/20
[52] U.S. Cl. .................................. 568/375; 568/821; 568/561; 568/327; 568/326; 568/808; 424/422; 549/505; 549/229

[58] Field of Search ............... 568/375, 821, 327, 326, 568/808, 561; 424/422

[56] References Cited

PUBLICATIONS

Darby, N. et al. J. Chem. Soc. D(23) 1516–1517 1971.

*Primary Examiner*—Paul J. Killos
*Attorney, Agent, or Firm*—Dressler, Goldsmith, Shore, Sutker & Milnamow, Ltd.

[57] ABSTRACT

Macrocyclic enediynediols and enediynediones having a ten carbon ring and open chain enediyne dihydroperoxides having eight carbons between the hydroperoxide groups that cleave DNA are disclosed, as are methods of making and using the same.

8 Claims, 1 Drawing Sheet

TEN-MEMBERED RING ENEDIYNEDIOLS AND ENEDIYNEDIONES HAVING DNA CLEAVING PROPERTIES

GOVERNMENTAL RIGHTS

This invention was made with support from the United States Government, and the United States Government has certain rights in the invention.

DESCRIPTION

1. Technical Field

The present invention relates to novel DNA-cleaving and antitumor compounds, and more specifically to a group of macrocyclic enediynediols, enediynediones having ten carbons in the ring and related open chain hydroperoxide compounds having eight carbons between the hydroperoxides that cleave DNA molecules.

2. Background Art

Natural products have been capturing the interest and imagination of isolation, synthetic, and medicinal chemists for a very long time due to their fascinating structures and biological activities. Man-designed molecules ("designer molecules") with predefined chemical and biological properties could enrich and complement this arsenal of substances, and sharpen the capability of chemistry to deliver biologically and therapeutically useful compounds.

Described herein are the design, synthesis, chemical and biological actions of novel designer molecules with DNA cleaving and antitumor properties; for some recent examples of designed DNA-cleaving molecules, see: (a) Nicolaou et al., *J. Am. Chem. Soc.*, 110:4866, 7247 (1988); (b) Nicolaou et al., *Angew. Chem. Int. Ed. Engl.*, 28:1272 (1989); (c) Povsic et al., *J. Am. Chem. Soc.*, 111:3059 (1989); (d) Hertzberg et al., *J. Am. Chem. Soc.*, 104:313 (1982); (e) Moser et al., *Science*, 238:645 (1987); (f) Corey et al., *J. Am. Chem. Soc.*, 111:8523 (1989); (g) Pyle et al., *J. Am. Chem. Soc.*, 111:4520 (1989); (h) Sigman, *J. Am. Chem. Soc.*, 111:4941 (1989); (i) Ohno et al., *J. Am. Chem. Soc.*, 112:0000 (1990); (j) Danishefsky, *J. Org. Chem.*, 54:2781 (1989); and Nicolaou et al., *Angew. Chem. Int. Ed. Engl.*, 103:1032 (1991).

In addition to the man-made DNA cleaving compounds, naturally occurring ene-diyne compounds have also been reported and studies. Included among the naturally occurring enediynes are calicheamicin and esperimicin that have substantially identical aglycon portions but different sugar portions [(a) Lee et al., *J. Am. Chem. Soc.*, 109:3464, 3466 (1987); (b) Nicolaou et al., *J. Am. Chem. Soc.*, 110:7247 (1988); (c) Hawley et al., *Proc. Natl. Acad. Sci. USA*, 86:1105 (1989); (d) Golik et al., *J. Am. Chem. Soc.*, 109:3461, 3462 (1987)] and neocarzinostation that also contains sugar-derivative side chains [(a) Edo et al., *Tetrahedron Lett.*, 26:331 (1984); (b) Chin et al. *Biochemistry*, 27:8106 (1988); (c) Lee et al., *Biochemistry*, 28:1019 (1989)].

BRIEF SUMMARY OF THE INVENTION

The invention contemplates novel DNA-cleaving, antibiotic and antitumor compounds that contain a macrocyclic 10-membered enediyne ring that includes two vincinal hydroxyl or keto (oxo) groups, as well as open chain hydroperoxides that can be prepared from the diketone upon photolysis with actinic light. The hydroperoxides have 8 carbons between the hydroperoxide groups. General structural formulas for the macrocyclic enediynediol compound, macrocyclic enediynedione compounds and open chain enediynedihydroperoxide compounds are shown below as formulas I, II and III, respectively.

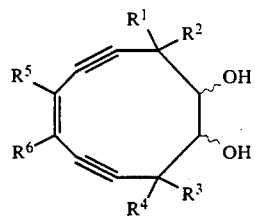

I

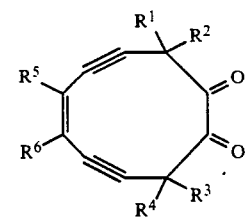

II

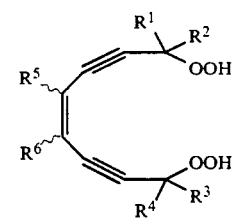

III wherein $R^1$, $R^2$, $R^3$ and $R^4$ are the same or different and are selected from the group consisting of hydrogen, $C_1$-$C_6$ alkyl, phenyl and benzyl with the provisos that only one of $R^1$ and $R^2$ and one of $R^3$ and $R^4$ is hydrogen;

$R^5$ and $R^6$ are both hydrogen, or $R^5$ and $R^6$ together with the unsaturated carbon atoms of the depicted vinylene group forms an aromatic monocyclic ring or a bicyclic fused ring system that includes six atoms in the ring containing the depicted vinylene group; and wavy lines are used to indicate that both cis and trans isomers are contemplated.

Compounds in which $R^5$ and $R^6$ are both hydrogen and $R^1=R^2=R^3=R^4=$methyl are particularly preferred.

A pharmaceutical composition that contains a before-defined compound present in a DNA-cleaving, or tumor growth-inhibiting amount dissolved or dispersed in a physiologically tolerable diluent is also contemplated.

A method utilizing a before-discussed composition containing a compound of structural formulas I or III is also contemplated. Here, DNA to be cleaved or target tumor cells whose growth is to be inhibited are contacted with a before-described composition. That contact is maintained for a time period sufficient for the desired result to be effected. Multiple administrations of the composition are also contemplated.

A photochemical method is also contemplated. Here, a pharmaceutical composition containing a macrocyclic enediynediketone compound of formula II is contacted with DNA to be cleaved or tumor cells to be killed to form a reaction mixture. That admixture is irradiated with actinic light in the presence of molecular oxygen for a time sufficient for the diketone to form an open chain enediyne dihydroperoxide containing eight carbon atoms separating the hydroperoxide groups as an active agent in a DNA-cleaving or tumor growth-inhibiting amount.

BRIEF DESCRIPTION OF THE DRAWINGS

In the drawings forming a portion of this disclosure.

DETAILED DESCRIPTION OF THE INVENTION

I. Introduction

Figure 1:
FIG. 1 is a photograph of an ethidium bromide stained 1 percent agarose electrophoresis gel that illustrates the cleavage of φX174 form 1 DNA by Compounds 2, 3, 4, 16b and 17b at 5000 μM after 48 hours at 50° C. at a pH value of 8.5. Lane 1 shows the DNA alone at pH 8.5 as control. Lanes 2-6 correspond to reactions carried out using Compounds 3, 2, 4, 17b and 16b, at pH values of 5.0, 6.0, 7.0, 7.4, 8.0, 8.5, 9.0, 9.5, 10.0 and 10.7, respectively. Forms I, II and III shown to the left of the photograph show the relative migrations of supercoiled (form I) relaxed (form II) and linear (form III) DNA, respectively.

The present invention relates to compounds, compositions and methods for cleaving DNA and thereby killing targeted cells such as tumor cells. Three related general types of compounds are contemplated.

The first is a macrocyclic enediynediol (sometimes referred to herein as a diol or vininal diol) that contains ten carbon atoms in the macrocyclic ring. These compounds can themselves cleave DNA.

The second is a macrocyclic enediynedione (sometimes referred to herein as a dione or vicinal dione) that can be prepared from an above diol and also contains ten carbon atoms in the macrocyclic ring. These compounds do not themselves cleave DNA to a great extent, but are precursors of hydroperoxide compounds that do cleave DNA. The diones can therefore be viewed as prodrugs for the hydroperoxide compounds.

Open chain enediyne hydroperoxides are the third type of contemplated compound. These compounds (sometimes referred to as hydroperoxides) contain eight carbons separating the hydroperoxides, and can be formed by photolysis (irradiation with actinic light) of the above diketones in the presence of molecular oxygen. The hydroperoxide compounds themselves also cleave DNA.

II. The Compounds

A diol of the invention has the structure shown below as formula I

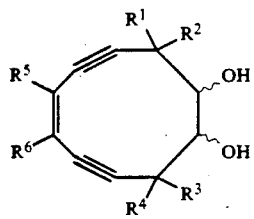

wherein
$R^1$, $R^2$, $R^3$ and $R^4$ are the same or different and are selected from the group consisting of hydrogen, $C_1$-$C_6$ alkyl, phenyl or benzyl, with the provisos that only one of $R^1$ and $R^2$ and one of $R^3$ and $R^4$ is hydrogen; and
$R^5$ and $R^6$ are each hydrogen or $R^5$ and $R^6$ together with the carbon atoms of the depicted vinylene group forms a group W that is an aromatic monocyclic ring or bicyclic fused ring system that includes five or six atoms in the ring containing the depicted vinylene group.

Both the cis and trans isomers of the diols are contemplated, and thus the bonds between the enediyne-containing macrocyclic ring and the hydroxyl (OH) groups are shown as wavy lines.

Where $R^5$ and $R^6$ together with the vinylene carbon atoms forms an aromatic ring system, a contemplated diol has the structure shown by formula Ia, below.

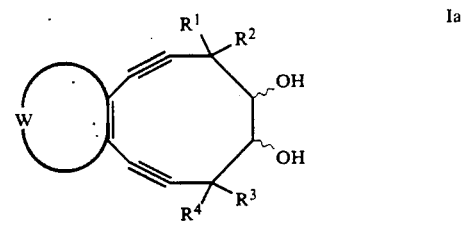

A diketone of the invention has the structure shown below as formula II, wherein $R^1$, $R^2$, $R^3$, $R^4$, $R^5$ and $R^6$ ($R^{1-6}$) are as defined above.

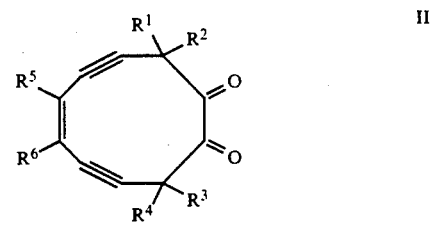

Where $R^5$ and $R^6$ together with the vinylene carbon atoms forms an aromatic ring system, a contemplated diketone has the structure shown by formula IIa, below.

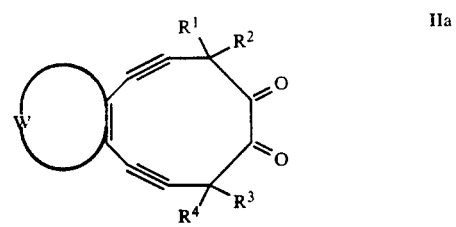

A hydroperoxide compound of the invention has the general structure shown below as formula III, wherein $R^{1-6}$ are as defined before, and the wavy lines linking $R^5$ and $R^6$ to the vinylene carbon atoms indicate that both cis and trans isomers are contemplated.

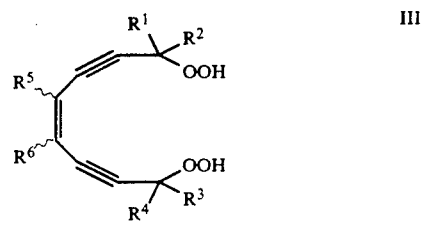

A general formula for a cis dihydroperoxide is shown below as formula IIIa. Where $R^5$ and $R^6$ together with the vinylene carbon atoms form an aromatic ring system, only the cis isomers are possible. Those compounds are shown generally below as formula IIIb.

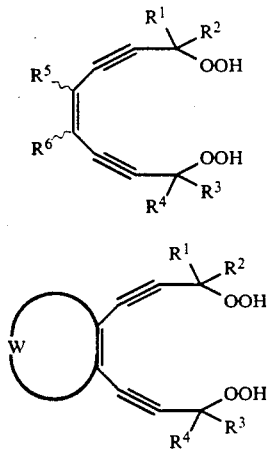

Compounds where $R^5$ and $R^6$ are both hydrogen are shown by formulas IIIc and IIId, below, respectively.

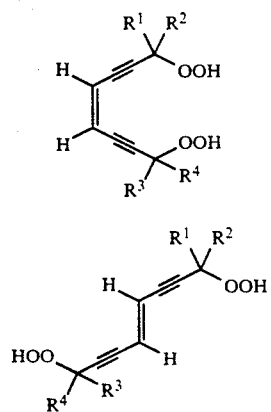

It is noted that the vinyl hydrogens are illustrated in formulas IIIc and IIIc. Those hydrogens and others not required to show stereochemistry, as where stereochemistry is shown by another group such as the hydroxyls of formula I or by usage of usual chemical bond notations, are omitted from subsequent structural formulas for purposes of clarity.

In examining the above structural formulas, it is noted first that only one of $R^1$ and $R^2$ or $R^3$ and $R^4$ is hydrogen. This preference relates particularly to the compounds of formulas II or III. The basis for this preference is that free radicals are believed to be formed in the photolysis of a compound of formula II and a secondary or tertiary carbon atom (the carbons linked to $R^1$ and $R^2$ or linked to $R^3$ and $R^4$) can more readily stabilize the free radical than can an unsubstituted carbon atom. Following the above preference, it is more preferred that both $R^1$ and $R^2$ and $R^3$ and $R^4$ be other than hydrogen.

A further preference as to $R^1$ and $R^2$ and $R^3$ and $R^4$ is that each pair be the same group; i.e., if $R^1$ is methyl, $R^2$ is methyl. The basis for this preference is ease of chemical synthesis in that if $R^1$ and $R^2$ (or $R^1$ and $R^4$) are different from each other, a chiral center could be formed that could require separation of enantiomers, whereas if $R^1=R^2$ and $R^3=R^4$, there would be no chirality.

A still further preference is that $R^1=R^2=R^3=R^4$. This preference also stems from ease of synthesis. Thus, if $R^1$ and $R^2$ are the same and $R^3$ and $R^4$ are the same, but $R^1$ and $R^3$ are different, complex mixture of products can be obtained that would require separation and loss of yield as to a particular compound. Thus, where $R^1=R^2=R^3=R^4$, the reaction mixture containing a compound with those groups is easier to deal with.

Turning now to the compounds wherein $R^5$ and $R^6$ together with the vinylene carbon atoms form an aromatic monocyclic or a bicyclic ring system W that includes five or six atoms in the ring containing the depicted vinylene group, e.g. formula I, several structures are contemplated.

Five- and six-membered aromatic ring systems include substituted and unsubstituted phenyl, furan, thiophene, pyridine, oxazole and pyrazine nucleii. Exemplary aromatic bicyclic ring systems include substituted and unsubstituted naphthalene, benzofuran, benzothiophene, isobenzofuran, isobenzothiophene, $C_1$-$C_6$ N-alkyl indole, $C_1$-$C_6$ N-alkyl isoindole, $C_1$-$C_6$ alkyl benzimidazole, quinoline, isoquinoline, benzoxazole and quinoxaline.

As noted above, the W ring system can have bonded to it, at various positions (other than those required for the fusion to the decadiynedione, decadiynediol ring or hydroperoxide-containing chain) a variety of substituents such as methyl, ethyl, isopropyl, n-propyl, isobutyl, sec-butyl, t-butyl, hexyl, and cyclohexyl ($C_1$-$C_6$ alkyl), methoxy, ethoxy, propoxy, butoxy, iso-butoxy, cyclopentyloxy, and cyclohexyloxy ($C_1$-$C_6$ alkoxy), perfluoromethyl, perfluoromethoxy, hydroxyl, $C_1$-$C_6$ acyloxy, benzyloxy, nitro, halo (fluoro, chloro, bromo and iodo), and amino having the formula $NR^7R^8$ wherein $R^7$ is selected from the group consisting of hydrogen (H), $C_1$-$C_6$ alkyl, benzyl, $C_1$-$C_6$ acyl and benzoyl, and $R^8$ is selected from the group consisting of hydrogen, $C_1$-$C_6$ alkyl and benzyl, or $NR^7R^8$ together form a 5- or 6-membered ring. A $C_1$-$C_6$ acyl groups is the carbonyl-containing residuum the reaction product of a $C_1$-$C_6$ carboxylic acid of an appropriate $C_1$-$C_6$ alkyl group above and an amine.

For ease of synthesis, because of the formation of isomeric products, it is preferred that a compound of formulas I–III include a plane of symmetry that can be drawn between the two alcohol (oxo or hydroperoxide) groups and bisecting the vinylene bond and any aromatic ring system W bonded thereto, with the cis-trans stereochemistry of the two hydroxyl groups being neglected. Thus, 5-membered ring compound derivatives such as those of the thiophene or furan are preferably bonded at the 3',4'-positions. Similarly, any substituents present on an aromatic ring system W are preferably symmetrically substituted about the depicted vinylene bond of formulas Ia, IIa or IIIb.

Of the above W ring systems, benzo and naphtho rings are preferred, with a benzo ring being more preferred. A substituted benzo ring is also contemplated, as are other substituted ring systems W, and 1–4 substituents can be bonded at the remaining positions not utilized in the fusion to the decadiyne macrocyclic ring. Those substituents can also be paired to form another fused aromatic ring. A structural formula for an exemplary compound is illustrated below.

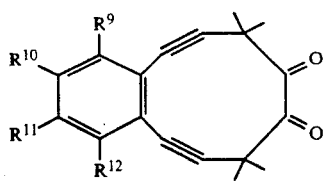

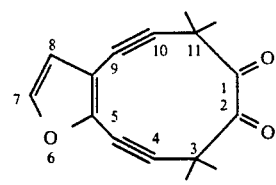

wherein $R^{1-4}$ are as defined before, and $R^9$, $R^{10}$, $R^{11}$ and $R^{12}$ are independently selected from a before-described substituent, or $R^9$ and $R^{10}$, $R^{10}$ and $R^{11}$ or $R^{11}$ and $R^{12}$ together with the depicted benzo ring form a fused bicyclic aromatic ring system.

In the case of an otherwise unsubstituted phenyl ring as W, the structure is symmetrical and therefore there is no possibility of isomers due to the nature of the phenyl ring. This is not the situation for heterocyclic structures such as furan or benzofuran. The fusion of furan as the W ring can be not only along the furan 2-3, 3-4, or 4-5 sides, but the oxygen can be on the same or the opposite side as the top of the macrocyclic cyclodecadiyne ring as shown. In order to avoid confusion with respect to how the fusion of these heterocyclic rings occurs, the convention that is used herein gives the ring position numbers of the heterocyclic ring (Chemical Abstract System) with the direction of the fusion given by a pair of numbers wherein the first of these numbers is the position next to the top of the cyclodecadiyne ring as shown.

For example, the numbering of the furan ring begins with the oxygen as 1', and the remaining numbers are assigned around the ring. Thus, the fusion can occur at the 3',4' bond, which would lead to a symmetrical structure. The 2',3' side, however, can be oriented so that the oxygen is either on the same or opposite side as the top of the shown structure in the adjoining enediyne ring. To differentiate these two possibilities, 3',2' indicates that the 3' position in the furan ring is bonded to a carbon atom at the top of the shown structure. Similarly, the designation 2',3' indicates that the 2' position is bonded to a carbon atom of the top of the structure shown. Thus, for any heterocyclic or asymmetric ring W fused to the cyclodecadiyndione ring, the first numeral of a fusion designation indicates an atom bonded to a carbon at the upper portion of the ring as shown herein.

The numbering of the entire fused ring system begins with a keto group in the upper right and continues clockwise to the next keto group and around the acetylenic ring, and then around the aromatic ring and back into the acteylenic ring. The bridgehead positions are not numbered since further substitution at these positions is not possible. The primed orientations that indicate the orientation of a heteroatom of an aromatic ring are parenthesized.

The structure for furano-(3',2')-cyclododeca4,9-diyne-1,2-dione is illustrated below with numbers adjacent to particular carbon atoms:

A diol is similarly named.

The following table illustrates various examples of H, and $C_1$–$C_6$ alkyl substituted diketone and diol compounds of this invention with the positions of the fused ring compounds having been numbered according to the Chemical Abstracts convention as illustrated above. Only the 3',4'- and 3',2'-fusions are illustrated for reasons of brevity.

| FUSED (3',4') and (3',2') FURAN DERIVATIVES | | | |
|---|---|---|---|
| Fusion | 6-Position | 7-Position | 8-Position |
| 3',4' | H | — | H |
| " | methyl | — | H |
| " | H | — | methyl |
| " | methyl | — | methyl |
| " | propyl | — | methyl |
| " | H | — | propyl |
| " | propyl | — | butyl |
| " | methyl | — | cyclohexyl |
| " | propyl | — | methyl |
| " | ethyl | — | H |
| " | H | — | ethyl |
| " | ethyl | — | pentyl |
| " | ethyl | — | ethyl |
| " | hexyl | — | propyl |
| " | methyl | — | ethyl |
| " | propyl | — | butyl |
| 3',2' | | H | H |
| " | | methyl | H |
| " | | H | methyl |
| " | | methyl | methyl |
| " | | ethyl | H |
| " | | H | ethyl |
| " | | pentyl | ethyl |
| " | | methyl | ethyl |
| " | | ethyl | methyl |
| " | | H | propyl |
| " | | propyl | H |
| " | | propyl | propyl |
| " | | cyclohexyl | methyl |
| " | | methyl | propyl |
| " | | propyl | ethyl |
| " | | ethyl | 2-methylbutyl |

In the above case, the substituents at positions 6, 7 and 8 can be all different, or all the same, and cannot only be H (hydrogen) or $C_1$–$C_6$ alkyl, as illustrated in the table, but can also be as discussed previously.

Examples of monoaromatic ring is fused systems are as follows:

| | | Position Number | | | |
|---|---|---|---|---|---|
| Aromatic Ring | Fusion | 9 | 9 | 10 | 11 |
| phenyl | 1',2' | x | x | x | x |
| furan | 3',4' | x | — | x | x |
| furan | 2',3' | — | x | x | x |
| furan | 3',2' | — | x | x | — |
| thiophene | 3',4' | x | — | x | — |
| thiophene | 2',3' | — | x | x | — |
| thiophene | 3',2' | — | x | x | — |
| pyridine | 3',2' | — | x | x | x |
| pyridine | 2',3' | x | x | x | — |
| pyridine | 3',4' | x | — | — | x |
| pyridine | 4',3' | x | — | x | x |

-continued

| Aromatic Ring | Fusion | Position Number | | | |
|---|---|---|---|---|---|
| | | 9 | 9 | 10 | 11 |
| oxazole | 4',5' | — | — | x | — |
| oxazole | 5',4' | x | — | — | — |
| oxazole | 3',4' | x | — | — | — |
| oxazole | 4',3' | — | — | x | — |
| pyrazine | 2',3' | — | x | x | — |
| pyrimidine | 5',6' | — | x | — | x |
| pyrimidine | 6',5' | x | — | x | — |
| pyridine | 2',3' | — | — | — | — |
| pyridine | 2',3' | — | x | — | — |
| pyridine | 2',3' | — | — | x | x |
| pyridine | 3',4' | — | — | x | — |
| pyridine | 3',2' | — | x | — | — |

The monoaromatic ring compounds listed in the table above have substituents (X) at positions, 8, 9, 10, and 11 that can all be the same or different, and are as discussed before.

The following table contains suitable derivatives based upon bicyclic aromatic ring systems as ring W;

| Aromatic Ring | Fusion | Position Number | | | | | |
|---|---|---|---|---|---|---|---|
| | | 8 | 9 | 10 | 11 | 12 | 13 |
| naphthalene | 6',7' | x | x | x | x | x | x |
| naphthalene | 5',6' | x | x | x | x | x | x |
| naphthalene | 6',5' | x | x | x | x | x | x |
| benzofuran | 2',3' | x | x | x | x | — | — |
| benzofuran | 3',2' | — | x | x | x | x | — |
| benzofuran | 5',6' | x | — | x | x | x | — |
| benzofuran | 6',5' | x | x | x | — | x | — |
| benzofuran | 6',7' | — | x | x | x | x | — |
| benzofuran | 7',6' | x | x | x | x | — | — |
| benzofuran | 4',5' | x | x | — | x | x | — |
| benzofuran | 5',4' | x | x | — | x | x | — |
| benzothiophene | 2',3' | x | x | x | x | — | — |
| benzothiophene | 3',2' | — | x | x | x | x | — |
| benzothiophene | 5',6' | x | — | x | x | x | — |
| benzothiophene | 6',5' | x | x | x | — | x | — |
| benzothiophene | 6',7' | — | x | x | x | x | — |
| benzothiophene | 7',6' | x | x | x | x | — | — |
| benzothiophene | 4',5' | x | x | — | x | x | — |
| benzothiophene | 5',4' | x | x | — | x | x | — |
| isobenzofuran | 5',6' | x | x | — | x | x | — |
| isobenzofuran | 4',5' | x | x | x | — | x | — |
| isobenzofuran | 5',4' | x | — | x | x | x | — |
| isobenzothiophene | 5',6' | x | x | — | x | x | — |
| isobenzothiophene | 4',5' | x | x | x | — | x | — |
| isobenzothiophene | 5',4' | x | — | x | x | x | — |
| N-methylindole | 3',2' | — | x | x | x | x | — |
| N-ethylindole | 2',3' | x | x | x | x | — | — |
| N-bytylindole | 5',6' | x | — | x | x | x | — |
| N-proylindole | 6',5' | x | x | x | — | x | — |
| N-cyclohexylindole | 4',5' | x | x | — | x | x | — |
| N-methylindole | 5',4' | x | x | — | x | x | — |
| N-iso-propylindole | 6',7' | — | x | x | x | x | — |
| N-pentylindole | 7',6' | x | x | x | x | — | — |
| N-methylisoindole | 5',6' | x | x | — | x | x | — |
| N-methylisoindole | 4',5' | x | x | x | — | x | — |
| N-methylisoindole | 5',4' | x | — | x | x | x | — |
| N-methylbenzimidazole | 5',6' | x | — | x | — | x | — |
| N-iso-pentylbenzimidazole | 6',5' | x | — | x | — | x | — |
| N-ethylbenzimidazole | 4',5' | x | x | x | — | — | — |
| N-pentylbenzimidazole | 5',4' | — | x | — | x | x | — |
| N-butylbenzimidazole | 6',7' | — | x | — | x | x | — |
| N-hexylbenzimidazole | 7',6' | x | x | — | x | — | — |
| guinoline | 2',3' | x | x | x | x | x | — |
| guinoline | 3',2' | — | x | x | x | x | x |
| guinoline | 3',4' | x | x | x | x | — | x |
| guinoline | 4',3' | x | — | x | x | x | x |
| guinoline | 5',6' | x | x | — | x | x | x |
| guinoline | 6',5' | x | x | x | — | x | x |
| guinoline | 6',7' | x | — | x | x | x | x |
| guinoline | 7',6' | x | x | x | x | — | x |
| guinoline | 7',8' | — | x | x | x | x | x |
| guinoline | 8',7 | x | x | x | x | x | — |
| isoguinoline | 3',4' | x | x | x | x | — | x |
| isoguinoline | 4',3' | x | — | x | x | x | x |
| isoguinoline | 6',7' | x | — | x | x | x | x |
| isoguinoline | 7',6' | x | x | x | x | — | x |
| benzoxazole | 4',5' | x | x | — | — | x | — |
| benzoxazole | 5',4' | x | — | — | x | x | — |
| benzoxazole | 5',6' | x | — | — | x | x | — |
| benzoxazole | 6',5' | x | x | — | — | x | — |
| benzoxazole | 6',7' | — | — | x | x | x | — |
| benzoxazole | 7',6' | x | x | x | — | — | — |
| guinoxaline | 2',3' | — | x | x | x | x | — |
| guinoxaline | 5',6' | x | x | — | x | x | — |
| guinoxaline | 6',5' | — | x | x | — | x | x |
| guinoxaline | 6',7' | x | — | x | x | — | x |

In the above table, the substituents (x) at positions 8 through 13, can be all different or all the same, and are as previously defined.

Reference is made herein to the carbon atoms of the vinylene group of depicted structural formulas. Following modern theories, those carbon atoms from sp² bonds. Atoms in aromatic W groups also form sp² bonds.

Thus, when $R^5$ and $R^6$ together with the carbon atoms of a depicted vinylene group form an aromatic ring system, W, the bonding of those carbon atoms of the depicted vinylene group remains sp². Nevertheless, usual structural formulas for aromatic compounds that utilize alternating double and single bonds can show a single bond rather than a double bond at the position occupied by a depicted vinylene group.

In view of the fact that the hybridization of the carbons of a depicted vinylene group remain sp², and such sp² hybridization rather than the presence of a vinylene group, per se, is what is of importance in the reactions of a compound of the invention, the absence of a "formalized", double bond in a written formula for a compound of formulas I, II or III, where W is present, is of no consequence. Where $R^5$ and $R^6$ are both hydrogen, a "formalized" double bond of the vinylene group is always present in a structural formula for a compound of formulas I-III.

In reviewing the above preferences it is seen that in particularly preferred practice, $R^1=R^2=R^3=R^4$. In addition, particularly preferred $R^{1-4}$ groups are methyl. It is also particularly preferred that $R^5$ and $R^6$ be hydrogen. Structural formulas for the particularly preferred cis and trans diols of Formula I (Compounds 2 and 3, respectively), the diketone of formula II (Compound 4), and the cis and trans hydroperoxides of formula III (Compounds 16b and 17b, respectively) are shown below, where bonds terminated by no group indicate methyl groups.

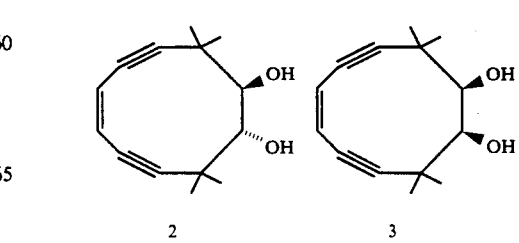

2   3

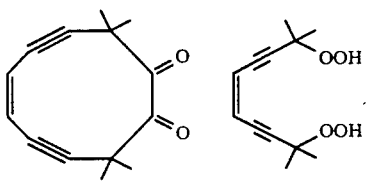

4    16b

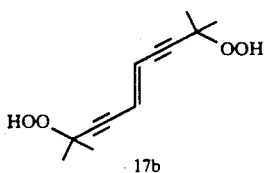

17b

III. Syntheses

A compound of the invention is prepared readily. A detailed description of the preparation of exemplary, preferred compounds 2, 3 and 4 is provided in Schemes 1 and 2 and adjoining text. The discussion that follows will therefore center on preparation of compounds where $R^5$ and $R^6$ together with the vinylene group carbon atoms forms an aromatic rings system W. In addition, the discussion below will stop at the vicinal diol stage inasmuch as the diketone is typically prepared from the vicinal diol, and the discussion relating to Scheme 2 illustrates diketone formation from a diol precursor.

In a preferred method of synthesis, the portions of the molecule containing the triple bonds are added separately or together to the vinylene-containing portion as hydroxyl-blocked $R^1$ and $R^2$ or (or $R^3$ and $R^4$) containing entities. The hydroxyls of the resulting endiyne compound are then deblocked, oxidized to aldehydes and the aldehydes are linked to form a cyclic diol.

As noted earlier, it is preferred that the whole molecule be symmetrical with a plane of symmetry running between the two alcohol (keto or hydroperoxide) groups and bisecting the vinylene group. As such, it is preferred that the two triple bond-containing portions be identical in which case the $R^1$ and $R^2$ groups are the same as the $R^3$ and $R^4$ groups. In view of the fact that difficultly separable stereoisomers can arise when $R^1$ and $R^2$ (or $R^3$ and $R^4$) are not identical, it is also preferred that $R^1$ and $R^2$ be identical and therefore that $R^1=R^2=R^3=R^4$, as noted before.

Notwithstanding the above preferences for a symmetrical diol and sameness of $R^{1-4}$, asymmetric, chiral molecules are also contemplated. Such molecules are, however, less preferred because of the difficulties involved with separation of the various isomers that can be produced.

Turning now to the blocked alcohol-acetylene-containing portions, exemplary starting materials are 2-substituted-propane-1,3-diols. Many of these diols are commercially available and others are readily prepared. For example, 2,2-dimethyl-1,3-propanediol (used as exemplary herein) and 2,2-diethyl-1,3-propanediol are available from Aldrich Chemical Co. of Milwaukee, Wis.

Asymmetrically mono-substituted propanediols can be conveniently prepared from malonic acid and its esters by reduction with lithium aluminum hydride, by dissolving metal reduction in the presence of an alcohol and by several other methods well known to those skilled in the art. Exemplary malonates such as diethyl butylmalonate, phenylmalonic acid and diethyl benzylmalonate are also available from Aldrich Chemical Co.

Further mono- and disubstituted malonate diesters can be readily prepared by alkylation of the diethyl malonate anion in the presence of base with a suitable alkylating agent. Such mono- and dialkylations of malonate diesters are also well known by workers skilled in synthetic organic chemistry. Reduction of the substituted malonates as discussed before provides the diol.

Once the appropriately substituted propane-1,3-diol is in hand, one of the hydroxyl groups is blocked with a base-insensitive blocking group such as a silane. Exemplary silane blocking groups include trialkylsilyl groups such as trimethyl, triethyl and t-butyldimethyl silyl groups. Alkylaryl silyl ($^t$BuPh$_2$Si) groups such as methyldiphenyl and t-butyldiphenyl silyl groups can also be used, as can other well known silane blocking groups.

The unprotected hydroxyl groups is then oxidized to form an aldehyde as by treatment with oxalyl chloride and DMSO followed by triethylamine. The resulting aldehyde oxygen is replaced by a CBr$_2$ group by reaction of the aldehyde with excess CBr$_4$ and triphenylphosphine [P(Ph)$_3$]. The resulting dibromo compound is then converted to the desired acetylene-blocked alcohol compound by reaction with a strong base such as methyl lithium.

The aromatic ring system portion of the molecule that provides the vinylene group shown in the various structures is typically provided by a vicinal dihalo-substituted aromatic compound. Again, many desirable starting materials are commercially available. A non-limiting list of exemplary compounds available from Aldrich Chemical Co. includes the following: 1,2-dichlorobenzene, 1,2-dibromobenzene, 1,2-diiodobenzene, 3,4-dibromothiophene, 3,4-dichlorotoluene, 2,3-dichlorotoluene, 2,3-dichloroquinoxaline, 2,3-dichloropyridine, 2,3-dichloroanisole.

Several vicinally dihalogenated anilines and nitrobenzene derivatives from which anilines and NR$^7$R$^8$ groups can be prepared by standard means are also available from Aldrich Chemical Co. Exemplary compounds include 2,3-dichloroaniline, 3,4-dichloroaniline, 4,5-dichloro-2-nitroaniline.

Vicinally dihalogenated phenols from which $C_1$–$C_6$ alkoxy substituted benzo derivatives can be readily prepared by well known means are also available from Aldrich Chemical Co. Exemplary of these are 2,3-dichlorophenol and 3,4-dichlorophenol.

The above lists are not intended to be exhaustive, but rather to illustrate the diversity of useful materials available from a single supplier. Other suitable vicinal dihalo aromatic compounds (and substituted propane-1,3-diols) can be obtained from other commercial suppliers, by reference to the chemical literature or by ready adaptation of a known syntheses to prepare a desired compound.

With the dihaloaromatic ring system compound that provides the depicted vinylene group in hand, preferably also including any desired substituent $R^{9-13}$ groups, and the acetylene-blocked alcohol portions also in hand, the dialcohol, open chain precursor to the desired macrocyclic diol can be prepared. For the purposes of clarity and brevity, preparation of a symmetrical molecule is discussed.

Thus, one equivalent of the vicinal dihaloaromatic ring system compound and two equivalents of the acetylene-blocked alcohol compound are reacted in the presence of a catalytic amount of a tetrakis(triphenylphosphine)palladium complex [Pd(PPh$_3$)$_4$], an excess of N-butylamine (nBuNH$_2$) and about 0.5 equivalents of cuprous iodide in benzene to join both acetylene-containing portions to the aromatic ring system compound. Removal of the alcohol blocking groups as with tetra-n-butylammonium fluoride [(nBu)$_4$NF], followed by oxidation with oxalyl chloride and DMSO and an excess of triethylamine provides the open chain, aromatic ring-containing dialdehyde.

Reaction of the open chain aromatic ring-system-containing dieynedialdehyde with excess samarium diiodide (SmI$_2$), or an excess of titanium metal [Ti(O)] provides a mixture of the cis and trans macrocyclic diols. The diols can be separated and utilized to cleave DNA or can be used without separation to form the macrocyclic diketones as is described hereinafter for the preparation of Compound 4, using the before discussed oxalyl chloride/DMSO oxidation.

IV. Pharmaceutical Compositions

A diol or hydroperoxide compound of the invention is useful as a DNA cleaving agent, as are dynemicin A, calicheamicin, esperimicin and neocarzinostatin. A compound of the invention can also therefore be referred to as an "active agent" or "active ingredient". A diol compound of the invention can also be used to inhibit the growth of neoplastic cells as can those known compounds in that DNA cleavage of tumor cells by those previously known compounds proceeds via DNA cleavage, at least in part. A hydroperoxide compound of the invention also cleaves DNA and can inhibit growth of tumor cells. A dione compound of the invention exhibits relatively poor DNA cleaving ability, but is useful as a "prodrug" for forming a contemplated hydroperoxide compound. Thus, a pharmaceutical composition of each of the compounds of each of formulas I, II and III is contemplated.

DNA cleavage can be assayed using the techniques described hereinafter as well as those described by Mantlo et al., *J. Org. Chem.*, 54:2781 (1989); Nicolaou et al., *J. Am. Chem. Soc.*, 110:7147 (1989); Nicolaou et al., *J. Am. Chem. Soc.*, 110:7247 (1988) or Zein et al., *Science*, 240:1198 (1988) and the citations therein.

A before-described diol compound can also be shown to undergo a Bergman cycloaromatization reaction in the presence of benzyl mercaptan, 1,4-cyclohexadiene or other hydrogen donor as discussed in Haseltine et al., *J. Am. Chem. Soc.*, 111:7638 (1989). This reaction forms a benzene-containing reaction product as is formed during DNA cleavage, and can be used as a co-screen to select more active compounds.

A pharmaceutical composition is thus contemplated that contains a before-described compound of the invention as active agent. A pharmaceutical composition is prepared by any of the methods well known in the art of pharmacy all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier or diluent.

A carrier or diluent is a material useful for administering the active compound and must be "pharmaceutically acceptable" in the sense of being compatible with the other ingredients of the composition and not deleterious to the recipient thereof. Thus, as used herein, the phrases "physiologically tolerable" or "pharmaceutically acceptable" are used interchangeably and refer to molecular entities and compositions that do not produce an allergic or similar untoward reaction, such as gastric upset, dizziness and the like, when administered to a mammal. The physiologically tolerable carrier can take a wide variety of forms depending upon the preparation desired for administration and the intended route of administration.

As an example of a useful composition, a compound of the invention (active agent) can be utilized, dissolved or dispersed in a liquid composition such as a sterile suspension or solution, or as isotonic preparation containing suitable preservatives. Particularly well-suited for the present purposes are injectable media constituted by aqueous injectable buffered or unbuffered isotonic and sterile saline or glucose solutions, as well as water alone, or an aqueous ethanol solution. Additional liquid forms in which these compounds can be incorporated for administration include flavored emulsions with edible oils such as cottonseed oil, sesame oil, coconut oil, peanut oil, and the like, as well as elixirs and similar pharmaceutical vehicles. Exemplary further liquid diluents can be found in *Remmington's Pharmaceutical Sciences*, Hack Publishing Co., Easton, Pa. (1980).

An active agent can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, pharmaceutically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods of forming liposomes are known in the art See, for example, Prescott, Ed., *Methods in cell Biology*, Vol. XIV, Academic press, New York, N.Y. (1976), p.33 et seq.

An active agent can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It should be understood that in addition to the aforementioned carrier ingredients the pharmaceutical composition described herein can include, as appropriate, one or more additional carrier ingredients such as diluents, buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

A compound of the invention is present in such a pharmaceutical composition in an amount effective to achieve the desired result. For example, where in vitro DNA cleavage is the desired result, a compound of the invention can be utilized in an amount sufficient to provide a concentration of about 1.0 to about 10,000 micromolar ($\mu$M) with a DNA concentration of about 0.02 $\mu$g/mL. As a cytoxic (antitumor) agent, an effective amount of a compound of the invention is about 0.1 to about 50 mg per kilogram of body weight or an amount sufficient to provide a concentration of about 0.01 to about 100 $\mu$g/mL to the bloodstream.

V. Methods

A compound of the invention is useful in cleaving DNA, and also in inhibiting the growth (killing) of neoplastic tumor cells, and is utilized in a method for effecting such a result. A compound of the invention is typically utilized in a before-described composition.

In accordance with such a method, DNA or target neoplastic tumor cells to be killed are contacted with a composition that contains a diol compound of the invention (active ingredient) present in an amount effective or sufficient for such a purpose, as discussed before, dissolved or dispersed in a physiologically tolerable (pharmaceutically acceptable) diluent. That contact is maintained for a time sufficient for the desired result to be obtained; i.e., DNA cleaved, or neoplastic cell growth inhibited.

Where the desired result is carried out in vitro contact is maintained by simply admixing the DNA or target cells with the composition and maintaining them together under the appropriate conditions of temperature and for cell growth to occur, as for control, untreated cells. Thus, a single admixing and contacting is typically sufficient for in vitro purposes.

The above method is also useful in vivo, as where a mammal such as a rodent like a rat, mouse, or rabbit, a farm animal like a horse, cow or goat, or a primate like a monkey, ape or human is treated. Here, contact of a composition and the cells to be killed via DNA cleavage is achieved by administration of the composition to the mammal by oral, nasal or anal administration or by introduction intravenously, subcutaneously or intraperitoneally. Thus, contact in vivo is achieved via the blood or lymph systems.

Although a single administration (admixture) and its resulting contact is usually sufficient to maintain the required contact and obtain a desired result in vitro, multiple administrations are typically utilized in vivo. Thus, because of a body's breakdown and excreting pathways, contact between an active ingredient of a composition and the target cells is typically maintained by repeated administration of a compound of the invention over a period of time such as days, weeks or months, or more, depending upon the target cells.

Exemplary methods of the invention for DNA cleavage are illustrated hereinafter.

In another embodiment of the invention, an effective amount of a vicinal diketone compound of the invention in an aqueous medium (a before-discribed composition) is admixed with DNA to be cleaved to form a reaction mixture. That reaction mixture is irradiated in the presence of molecular oxygen with actinic light, e.g. about 280–400nm for a time period sufficient to form an amount of a before-described hydroperoxide effective to cleave DNA.

Such irradiation causes cleavage of the diketone and formation of an enediyne dihydroperoxide whose —OOH (hydroperoxide) groups are linked to the carbon atom(s) bonded to the $R^1$ and $R^2$ (and/or $R^3$ and $R^4$) groups and are separated by eight carbon atoms. The elements of two moles of carbon monoxide [O=C=C=O; ethylenedione] are thus eliminated from the diketone precursor.

The previous remarks concerning a diol active agent are applicable to the above method using a diketone compound of the invention.

A particular advantage of the above photoactivation method is that the effects of the active agent hydroperoxide can be relatively localized in an in vivo situation. Thus, whereas a diol compound of the invention or a known enediyne acts systemically once administered, a diketone compound as active agent does not itself cleave DNA effectively. Rather, the compound must be activated to do so by irradiation.

As a result of the photoactivation, the effects of the radiation-produced hydroperoxide tend to be localized more closely to the areas of the host animal such as a mouse, rat, pig or human, through which the actinic light can pass; i.e., the skin.

VI. Results

Molecules 2–4 (shown previously) were targeted for synthesis for their novel structures and potential chemical and biological properties. Compounds 2–4 were prepared by the route shown below in Schemes 1 and 2. (It is noted that the R and subscripted R groups used in the schemes that follow have the meanings shown in the schemes as compared to the prior definitions for superscripted R groups.)

Scheme 1

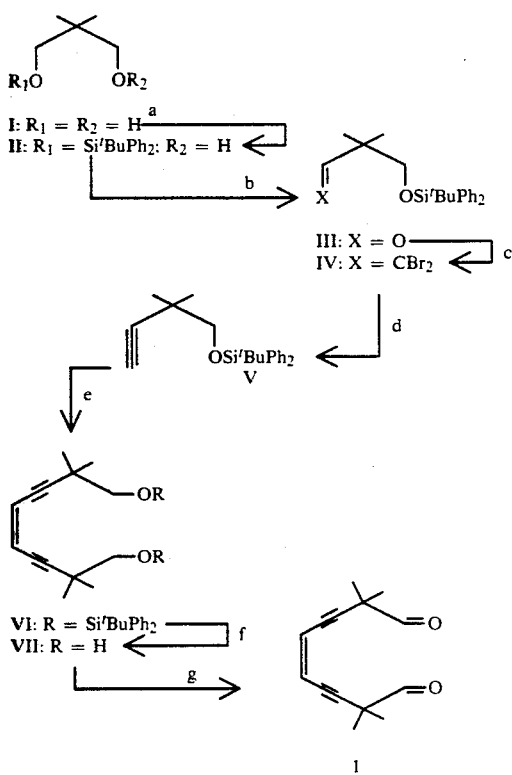

In reference to Scheme 1, one equivalent of 2,2-dimethyl-1,3-propanediol (Compound I) was reacted with 0.1 equivalents of t-butyldiphenylsilyl chloride ($^t$BuPh$_2$SiCl) and 0.2 equivalents of imidazole in DMF at zero degrees C. for 20 minutes to form the monoalcohol blocked Compound II in 88 percent yield in step a. One equivalent of Compound II was then reacted with 1.2 equivalents of oxyalyl chloride and 1.5 equivalents of DMSO at a temperature of −78° C. for 30 minutes. The reaction mixture was then treated with 4.0 equivalents of triethylamine (Et$_3$N) at −78° C., and permitted to warm to room temperature in step b to provide Compound III in 95 percent yield.

One equivalent of Compound III was reacted with 2.2 equivalents of tetrabromomethane (CBr$_4$) and 4.4 equivalents of triphenylphosphene (PPh$_3$) in dichloromethane at zero degrees C. for 30 minutes in step c to form Compound IV in 88 percent yield. The latter compound was reacted with 2.2 equivalents of methyl lithium (MeLi) at a temperature of −78° C. for 30 minutes to provide the acetylene-blocked hydroxyl Compound V in 82 percent yield as step d.

One equivalent of Compound V was reacted with 0.5 equivalents of cis-1,2-dichloroethylene, 0.07 equivalents of a palladium triphenylphosphene complex [Pd(PPh$_3$)$_4$], 2.0 equivalents of n-butylamine (nBuNH$_2$) and 0.3 equivalents of cuprous iodide (CuI) in benzene at 25° C. for 10 hours in step e to provide Compound VI in 92 percent yield.

Cleavage of the blocking groups of Compound VI by reaction with 2.2 equivalents of tetra-n-butylammonium fluoride (nBu$_4$NF) in THF at 25° C. for four hours in step f provided the open chain diol Compound VII in 95 percent yield. Oxidation of Compound VII using 4.0 equivalents of oxalyl chloride and 6.0 equivalents of DMSO at −78° C. for 30 minutes followed by 10 equivalents of Et$_3$N at 25° C. for 30 minutes in step g provided the open chain dialdehyde Compound 1 in 92 percent yield.

Scheme 2

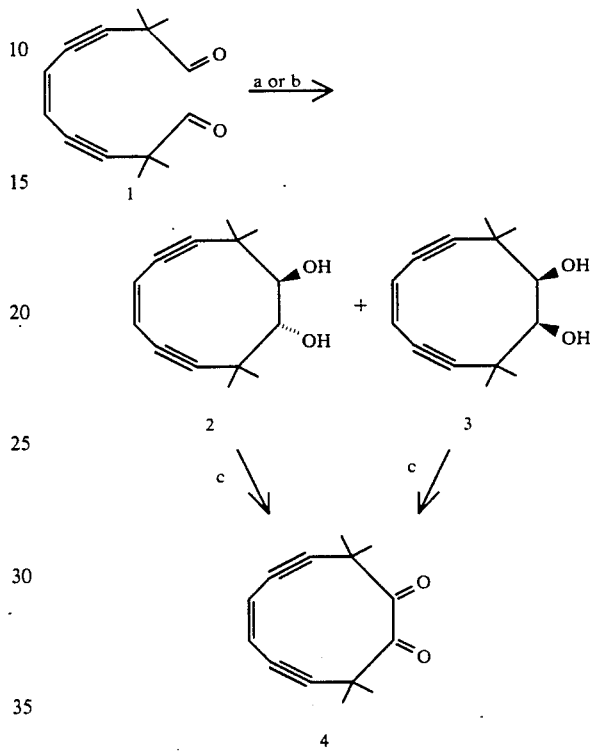

Scheme 2 illustrates the preparation of Compounds 2, 3 and 4. Thus, treatment of open chain dialdehyde Compound 1 with samarium diiodide in step a [for a review on the use of samarium diiodide in organic synthesis, see: Soderquist, Alrichchimica Acta, 24:15 (1991)] in THF at ambient temperature (about 25° C.) for one hour resulted in the formation of trans diol Compound 2 as the major product contaminated with a small amount of the cis isomer, Compound 3 (42 percent total yield, trans:cis, about 20:1, separated by flash column chromatography). On the other hand exposure of Compound 1 to an excess of McMurry's reagent in step b [Ti(O)-DME; (McMurray et al., J. Org. Chem., 54:3748 (1989); McMurray et al , Tetrahedron Lett., 30:1169 (1989)] in DME at ambient temperature for 12 hours led to a mixture in which the cis isomer was predominating (45 percent total yield, trans:cis, about 1:2.6).

The stereochemical assignment of the conformationally rigid Compounds 2 and 3 were based on NMR spectroscopic data and were confirmed by X-ray crystallographic analysis on one of them. [Inspection of molecular models of Compounds 2 and 3 revealed one distinctly preferred conformation for each compound. The trans isomer was comfortable in a conformation in which the two hydroxyl protons and the two protons adjacent to the oxygens were approximately equivalent due to their orientation in relation to the ring. On the contrary, the cis isomer sank into a conformation in which the orientations of these protons were distinctly different with respect to the enediyne moiety. This realization taken together with the apparent rigidity of these conformations led us to assign the simplest $^1$H NMR spectrum (5 signals) to the trans isomer and the more complex (8 signals) spectrum to the cis compound.] Frozen conformations of arrays of this type of adjacent stereocenters are rare and represent fascinating stereochemical phenomena.

Swern oxidation of either the trans or the cis vicinal diol, Compounds 2 or 3, led smoothly to the expected 1,2-dione, Compound 4, in 84–90 percent yield in step c. Molecular modeling suggested a nearly orthogonal arrangement of the two carbonyl groups in Compound 4, an inference supported by its IR spectrum. [Compound 4 exhibited a C=O band at $\lambda_{max}$ (neat) 1720 cm$^{-1}$ revealing no conjugation between the two carbonyl groups.

The Bergman reaction profiles of these enediynes were then examined as is illustrated in Scheme 3, below. Both Compounds 2 and 3 (shown in boxes in Scheme 3) were found to undergo smooth cycloaramatization in the presence of a hydrogen atom source at temperatures ranging from abient to 100° C. according to Scheme 3 to form Compounds 6 to 8, as shown in step a.

Compounds 6 to 8 were prepared in 50 to 49 percent yields from Compounds 2 and 3, respectively. The Bergman cycloaromatization reactions were carried out for both compounds using a solvent of benzene/1,4-cyclohexadiene (3:1, v:v) at a temperature of 80° C. for 12 hours (step a). Bergman products 6 and 8 are presumed to arise via the bracketed diradical intermediate Compounds 5 to 7, respectively.

Interestingly, the cis isomer cyclized faster (half-life at 50° C. in toluene-d$_8$, about four hours) than the trans isomer (half-life at 50° C. in toluene-d$_8$, about 22 hours). This observation may be explained by a higher energy barrier for the "flip" necessary prior to Bergman cyclization for the trans as compared to the corresponding barrier for the cis compound.

To increase this barrier even further, it was decided to constrain the two hydroxyl groups of Compound 2 within a ring which was expected to provide a "locking device", preventing cycloaromatization. Reaction of Compound 2 with oxalyl chloride in the presence of triethylamine at zero degrees C. resulted, oddly enough, in the formation of carbonate Compound 9 in 90 percent yield as a stable crystalline solid. Indeed this compound proved to be quite stable at 100° C. for several hours.

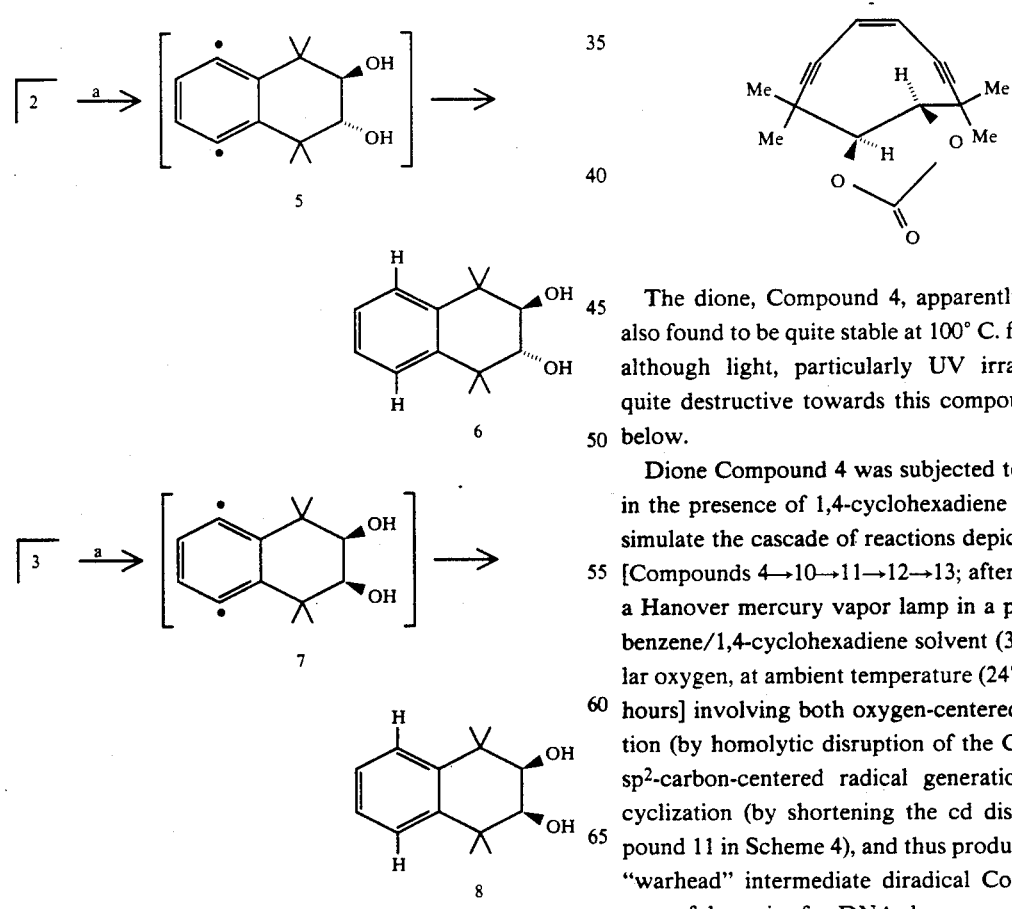

The dione, Compound 4, apparently "locked", was also found to be quite stable at 100° C. for several hours, although light, particularly UV irradiation, proved quite destructive towards this compound as discussed below.

Dione Compound 4 was subjected to UV irradiation in the presence of 1,4-cyclohexadiene in an attempt to simulate the cascade of reactions depicted in Scheme 4 [Compounds 4→10→11→12→13; after irradiation with a Hanover mercury vapor lamp in a pyrex vessel, in a benzene/1,4-cyclohexadiene solvent (3:1, v:v), molecular oxygen, at ambient temperature (24°→60° C.) for 0.5 hours] involving both oxygen-centered radical generation (by homolytic disruption of the C=O bonds) and sp$^2$-carbon-centered radical generation via Bergman cyclization (by shortening the cd distance, see Compound 11 in Scheme 4), and thus producing the multiple "warhead" intermediate diradical Compound 12 as a powerful species for DNA damage.

Scheme 4

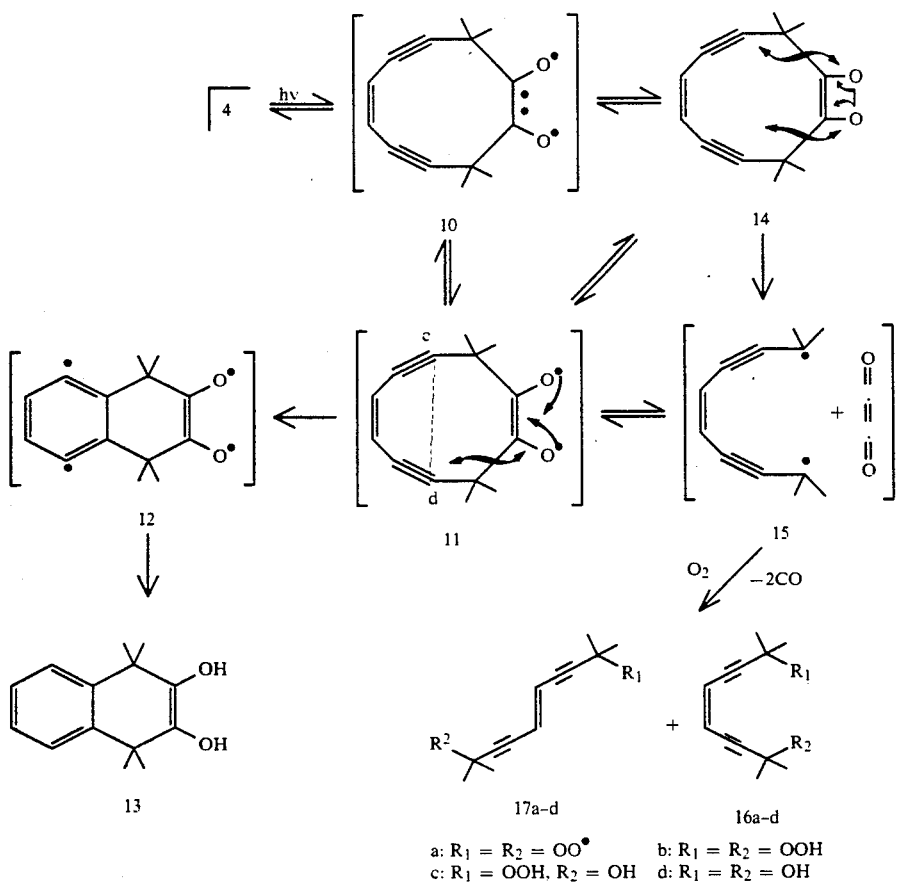

a: $R_1 = R_2 = OO^\bullet$  b: $R_1 = R_2 = OOH$
c: $R_1 = OOH, R_2 = OH$  d: $R_1 = R_2 = OH$ In the event, however, none of the expected Compound 13 was formed, but instead, the two novel dihydroperoxides, Compounds 16b and 17b, that were smoothly and sequentially converted to monohydroperoxides 16c and 17c and diols 16d and 17d upon treatment with excess dimethyl sulfide. The same transformations were effected, although less cleanly, by thermolysis in the presence of hydrogen atom donors.

Monohydroperoxide Compound 17c revealed a coupling constant J=15.4 Hz for the two olefinic protons leading to the trans assignment for the major series of Compound 17b-d and, by deduction, to the cis assignment for the minor isomers of Compounds 16c-d. Apparently, a second cascade of reactions is preferred, possibly involving Compounds 10, 11, 14 and 15 (Scheme 4).

Quite intriguing is the possibility of the intermediacy of dioxetene Compound 14 [a similar dioxetene system has been previously postulated by Turro and Krebs: Turro et al., J. Am. Chem. Soc., 98:6758 (1976). For a theoretical discussion on dioxetenes, see: Budzelaar et al., J. Am. Chem. Soc., 109:6290 (1987)] which is presumed to eject the equivalent of ethylenedione (decomposing to two molecules of carbon monoxide) and/or two carbon monoxide molecules and the stabilized diradical Compound 15 that proceeds to react with two molecules of oxygen to afford the observed products Compounds 16b and 17b (after isomerization) via diradical Compound 16a. [The existence of ethylenedione is debatable, see: Rubin et al., Tetrahedron Lett., 29:6641 (1988); Birney et al., Tetrahedron Lett., 42:1561 (1986); Raine et al., J. Am. Chem. Soc., 105:194 (1983).]

Vicinal diol compounds 2 and 3 caused significant DNA cleavage when incubated with φX174 supercoiled DNA at pH 8.5 and 50° C. (FIG. 1). Interestingly, the vicinal dione Compound 4 caused only slight DNA damage under the same conditions, whereas hydroperoxide Compounds 16b and 17b showed, as expected, quite strong DNA cleaving activities.

From the chemistry of these systems it is believed that, whereas the 10-membered ring enediynediol Compounds 2 and 3 exert their DNA cleaving power via a Bergman cyclization, the open-chain enediyne dihydroperoxide Compounds 16b and 17b operate via an entirely different mechanism involving the generation of oxygen centered radicals.

EXAMPLE 1: DNA CLEAVAGE STUDIES

To a vial containing a 50 micromolar per base pair solution of φX174 Type I double-stranded DNA in 2.0 microliters of various buffers whose pH values are shown in FIG. 1, e.g., pH 8.5 tris-HCl, were added 6.0 microliters of the same buffer solution and 2.0 microliters of a 5.0 millimolar ethanol solution of Compounds 2, 3, 4, 16b and 17b.

The vials were then placed in a 50° C. oven for 48 hours. A 2.0 microliter portion of glycerol loading buffer solution containing bromothymol blue indicator was added to each vial. A 10 microliter aliquot was then drawn from each. Gel electrophoresis analysis of the aliquots was performed using a 1.0 percent agarose gel with ethidium bromide run at 115 volts for one hour. DNA cleavage was indicated by the formation of Type II DNA, which was detected by visual inspection of the gel under 310 nanometer ultraviolet light.

EXAMPLE 2: PHYSICAL PROPERTIES OF SELECTED COMPOUNDS

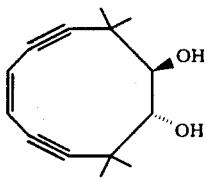
2

Compound 2: $R_f$: 0.42 (30 percent ether in petroleum ether); 32 percent yield; mp=100° C. (decomp.) IR (CHCl$_3$)$\nu_{max}$ 3500, 3025, 2400, 2280, 1650 cm$^{-1}$; $^1$H NMR (500 MHz, CDCl$_3$)δ5.79 (s, 2 H, olefinic), 4.03 (s, 2 H, CHO), 2.83 (bs, 2 H, OH), 1.31 (s, 6 H, CH$_3$), 1.12 (s, 6 H, CH$_3$); $^{13}$C NMR (125 MHz, CDCl$_3$)δ122.5, 107.4, 82.7, 76.8, 38.2, 26.5, 18.4; HRMS Calcd. C$_{14}$H$_{18}$O$_2$Na (M+Na), 241.1205, found 241.1212.

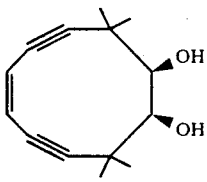
3

Compound 3: $R_f$: 0.40 (30 percent ether in petroleum ether): 42 percent yield; mp=90° C. (decomp.) IR (CHCl$_3$)$\nu_{max}$ 3500, 3015, 2125, 1602 cm$^{-1}$; $^1$H NMR (500 MHz, CDCl$_3$)δ5.81 (s, 2 H, olefinic), 4.00 (bd, 1 H, CHO), 3.38 (dd, J=13.5, 3.9 Hz, 1 H, CHO), 2.94 (d, J=13.5 Hz, 1 H, OH), 1.84 (bs, 1 H, OH), 1.38 (s, 6 H, 2×CH$_3$), 1.32 (s, 3 H, CH$_3$), 1.31 (s, 3 H, CH$_3$); HRMS Calcd. C$_{14}$H$_{18}$O$_2$Na (M+Na), 241.1205, found 241.1205

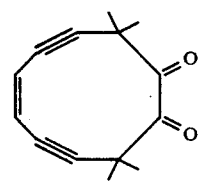
4

Compound 4: $R_f$: 0.25 (petroleum ether); 85 percent yield; IR (neat)$\nu_{max}$ 3000, 2175, 1720 cm$^{-1}$ $^1$H NMR (5000 MHz, CDCl$_3$)δ5.79 (s, 2 H, olefinic), 1.55 (bs, 12 H, 4×CH$_3$); $^{13}$C NMR (125 NMz, CDCl$_3$)δ200.9, 122.8, 101.6, 85.8, 43.2, 25.1; HRMS Calcd. C$_{16}$H$_{14}$O$_2$ (M), 241.0994, found 241.0995.

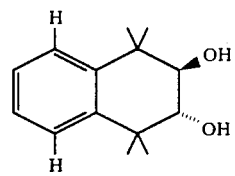
6

Compound 6: $R_f$: 0.47 (30 percent ether in petroleum ether); 49 percent yield; mp=123°-125° C.; IR (CHCl$_3$)$\nu_{max}$ 3510, 3450, 3012, 1500 cm$^{-1}$; $^1$H NMR (500 MHz, CDCl$_3$)δ7.32 (m, 2 H, aromatic), 7.18 (m, 2 H, aromatic), 3.86 (s, 2 H, 2×CHO), 1.90 (bs, 2 H, 2×OH), 1.41 (s, 6 H, 2×CH$_3$), 1.38 (s, 6 H, 2×CH$_3$); $^{13}$C NMR (125 MHz, CDCl$_3$)δ142.5, 126.6, 126.5 74.5, 40.2, 28.5, 25.8; HRMS Calcd. C$_{14}$H$_{20}$O$_2$Na (M+Na), 243.1361, found 243.1362.

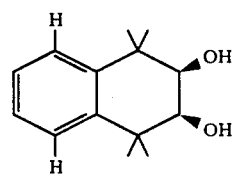
8

Compound 8: $R_f$: 0.35 (30 percent ether in petroleum ether); 50 percent yield; mp=143°-145° C.; IR (CHCl$_3$)$\nu_{max}$ 3560, 3310, 3000, 1510 cm$^{-1}$; $^1$H NMR (500 MHz, CDCl$_3$)δ7.31 (m, 2 H, aromatic), 7.19 (m, 2 H, aromatic), 3.89 (s, 2 H, CHO), 1.86 (bs, 2 H, 2×OH), 1.45 (s, 6 H, 2×CH$_3$), 1.31 (s, 6 H, 2×2×CH$_3$); $^{13}$C NMR (125 MHz, CDCl$_3$)δ142.6, 126.8, 126.4, 76.8, 39.7, 243.1355.

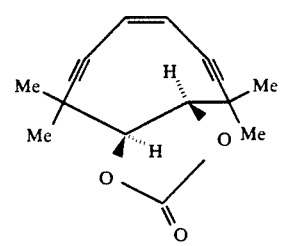
9

Compound 9: $R_f$: 0.55 (5 percent ether in petroleum ether); 83 percent yield; mp=132°-134° C.; IR (CHCl$_3$)$\nu_{max}$ 3042, 2190, 1762 cm$^{-1}$; $^1$H NMR (500 MHz, CDCl$_3$) δ5.87 (s, 2 H, olefinic), 4.64 (s, 2 H, 2×CHO), 1.43 (s, 6 H, 2×CH$_3$), 1.24 (s, 6 H, 2×CH$_3$); $^{13}$C NMR (125 MHz, CDCl$_3$)δ154.0, 123.0, 103.2, 84.4, 84.0, 36.3, 26.1, 18.4; HRMS Calcd. C$_{15}$H$_{16}$O$_3$Na (M+Na), 267.0997, found 267.0988; HRMS Calcd. C$_{15}$H$_{16}$O$_3$H (M+H), 245.1178, found 245.1170.

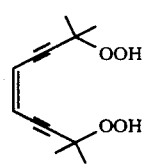
16b

Compound 16b: $R_f$: 0.32 (15% EtOAc in benzene); 10 percent yield; IR (neat)$\nu_{max}$ 3600, 3015, 2380, 1510 cm$^{-1}$; $^1$H NMR (500 MHz, CDCl$_3$)δ8.31 (bs, 2 H, 2×OOH), 5.89 (s, 2 H, 2×olefinic), 1.56 (s, 12 H, 4×CH₃); ¹³C NMR (125 MHz, CDCl₃)δ119.7, 98.2, 81.6, 78.2, 26.2; HRMS Calcd. C₁₂H₁₆O₄(M), 224.1049, found 224.1056.

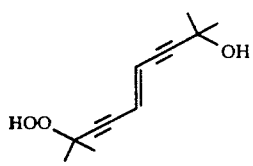

17b

Compound 17b: R_f: 0.30 (15 percent EtOAc in benzene); 20% yield; IR (neat)ν_max 3450, 3010, 2200 cm⁻¹; ¹H NMR (500 MHz, CDCl₃)δ7.83 (bs, 2 H, 2×OOH), 6.16 (s, 2 H, olefinic, 1.53 (s, 12 H, 4×CH₃); ¹³C NMR (125 MHz, CDCl₃)δ120.8, 95.2, 82.1, 78.0, 26.2; HRMS Calcd. C₁₂H₁₆O₄ (M), 224.1049, found 224.1052.

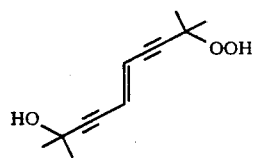

17c

Compound 17c: R_f: 0.28 (15 percent EtOAc in benzene); 45 percent yield; IR (neat)ν_max 3330, 3000, 2185, 1465 cm⁻¹; ¹H NMR (500 MHz, CDCl₃)δ7.80 (bs, 1 H, OOH), 5.98 (d, J=15.4 Hz, 1 H, olefinic), 5.93 (d, J=15.4 Hz, 1 H olefinic), 3.50 (bs, 1 H, OH), 1.53 (s, 6 H, 2×CH₃), 1.51 (s, 6 H, 2×CH₃); HRMS Calcd. C₁₂H₁₆O₃ (M), 208.1099, found 208.1099.

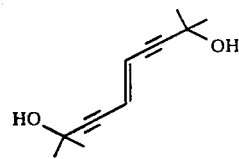

17d

Compound 17d: R_f: 0.26 (15 percent EtOAc in benzene); 96 percent yield; IR (neat)ν_max 3400, 3000, 1415 cm⁻¹; ¹H NMR (500 MHz, CDCl₃)δ5.93 (s, 2 H, olefinic), 3.40 (bs, 2 H, 2×OH), 1.52 (s, 12 H, 4×CH₃); HRMS Calcd. C₁₂H₁₆O₂(M), 192.1150, found 192.1138.

Although the present invention has now been described in terms of certain preferred embodiments, and exemplified with respect thereto, one skilled in the art will readily appreciate that various modifications, changes, omissions and substitutions may be made without departing from the spirit thereof.

We claim:

1. A compound of the formula

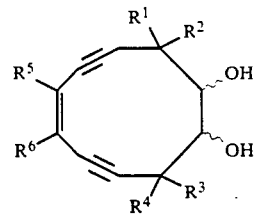

wherein
R⁵ and R⁶ are each hydrogen or R⁵ and R⁶ together with the carbon atoms of the depicted vinylene group forms a group W that is an aromatic monocyclic ring or bicyclic fused ring system that includes five or six atoms in the ring containing the depicted vinylene group; and
R¹, R², R³ and R⁴ are the same or different and are selected from the group consisting of hydrogen, C₁-C₆ alkyl, phenyl or benzyl, with the provisos that only one of R¹ and R² and one of R³ and R⁴ is hydrogen.

2. The compound of claim 1 wherein R⁵ and R⁶ and hydrogens.

3. The compound of claim 2 wherein R¹, R², R³ and R⁴ are each methyl.

4. The compound of claim 3 wherein the two depicted hydroxyl groups are cis.

5. The compound of claim 3 wherein the two depicted hydroxyl groups are trans.

6. A compound of the formula

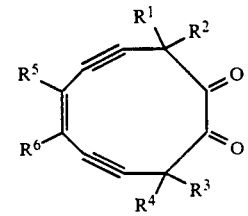

wherein
R⁵ and R⁶ are each hydrogen or R⁵ and R⁶ together with the carbon atoms of the depicted vinylene group forms a group W that is an aromatic monocyclic ring or bicyclic fused ring system that includes five or six atoms in the ring containing the depicted vinylene group; and
R¹, R², R³ and R⁴ are the same or different and are selected from the group consisting of hydrogen, C₁-C₆ alkyl, phenyl or benzyl, with the provisos that only one of R¹ and R² and one of R³ and R⁴ is hydrogen.

7. The compound of claim 6 wherein R⁵ and R⁶ and hydrogens.

8. The compound of claim 6 wherein R¹, R², R³ and R⁴ are each methyl.

* * * * *